US011365398B2

(12) United States Patent
Knight

(10) Patent No.: US 11,365,398 B2
(45) Date of Patent: *Jun. 21, 2022

(54) VIRUS PURIFICATION

(71) Applicant: CC Biotech LLC, Rockville, MD (US)

(72) Inventor: Martha Knight, Washington, DC (US)

(73) Assignee: CC Biotech LLC, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/106,135

(22) Filed: Nov. 29, 2020

(65) Prior Publication Data

US 2021/0079361 A1 Mar. 18, 2021

Related U.S. Application Data

(63) Continuation of application No. 16/289,608, filed on Feb. 28, 2019, now Pat. No. 10,851,349.

(60) Provisional application No. 62/636,827, filed on Feb. 28, 2018.

(51) Int. Cl.

| | |
|---|---|
| *C12N 7/00* | (2006.01) |
| *B01D 15/18* | (2006.01) |
| *B01D 15/42* | (2006.01) |

(52) U.S. Cl.

CPC .......... *C12N 7/00* (2013.01); *B01D 15/1807* (2013.01); *B01D 15/1892* (2013.01); *B01D 15/424* (2013.01); *C12N 2710/10051* (2013.01)

(58) Field of Classification Search
CPC ........... B01D 15/1807; B01D 15/1892; B01D 15/424; C12N 15/8245; C12N 2710/10051; C12N 7/00; C12N 2750/14151; C12N 15/101; C12N 15/02
See application file for complete search history.

(56) References Cited

U.S. PATENT DOCUMENTS

| | | | |
|---|---|---|---|
| 6,989,264 | B2 | 1/2006 | Atkinson et al. |
| 8,597,509 | B2 | 12/2013 | Knight et al. |
| 9,713,778 | B2 | 7/2017 | Knight et al. |

OTHER PUBLICATIONS

Ito et al., J Chrom Sci 51(7)726, 2013.
Huang et al., J Sep Sci 40:336, 2017.
Knight et al., J Chrom A 1218:6148, 2011.

*Primary Examiner* — Bao Q Li

(74) *Attorney, Agent, or Firm* — MDIP LLC

(57) ABSTRACT

A spiral tube countercurrent chromatography rotor for separating virus in a two part aqueous solvent is described.

18 Claims, 7 Drawing Sheets

VIRUS PURIFICATION

BACKGROUND OF THE INVENTION

Nucleic acid therapeutics encapsulated in viral vectors hold great hope for many diseases, especially those of point mutations or monogenic disorders, many designated as orphan diseases. In November 2017, successful clinical trials were announced for AveXis® (Avexis Corp., Dallas, Tex.) gene therapy for spinal muscular atrophy type 1 disease in infants. The AAV-based therapy injected a healthy copy of the SMN1 gene. Approval is on the way for LUXTURNA® (Spark Therapeutics, Philadelphia, Pa.), a genetic therapy treatment for blindness, and Biomarin with Spark has a therapy for hemophilia. Earlier in the year, there were FDA approvals of Kymriah (Novartis, Basel, CH) which treats leukemia and YESCARTA® (Kite Pharma, Santa Monica, Calif.) which treats a form of lymphoma. There are 300 trials ongoing on in the industry. The therapeutic potential is even broader, applicable for common conditions of infectious disease, cancer and addictive disorders.

A promising delivery vehicle for genetic therapy include viral particles or virus-like particles (VLP). The biotechnology industry is heavily involved in developing that therapeutic approach for many diseases, especially those caused by mutations, as well as use as vaccine for infectious diseases. VLP's are high MW species with subunits that self-assemble. Large molecule purification of molecules of the downstream process poses special challenges. The methods have to avoid denaturation and the nucleic acid protein complex has to be separated from side products, including the unfilled capsid. Most methods being adopted include affinity chromatography and membrane separation. A problem in applying column chromatographic methods, such as, ion exchange and size exclusion chromatography (SEC), is dilution, low recovery of the molecules and loss of activity. Currently, the most reliable separation method, density gradient ultracentrifugation, is difficult to perform in larger scale.

Isolation of nucleic acid-associated nanoparticles is a difficult problem in biotechnology and nanotechnology. For gene therapy applications, the virus protein capsid is important to transport the nucleic acid to a cell target. In the production of viable VLP it is necessary to separate the filled virus particle from the empty capsid, excess nucleic acid, host cell proteins and aggregated particles. Isolation of protein product from the fermentation reaction mixture requires many processing steps, lysis, centrifugation, ultrafiltration, tangential flow filtration, affinity resins that are expensive, a chromatographic polishing step (usually ion exchange chromatography) that still produces an sodium dodecyl sulfate-polyacrylamide gel electrophoresis (PAGE) analysis of the target protein with significant impurities; and so on. For high volumes, those processes are even more challenging and time consuming. Cutting down on the steps for isolation and purification will save time and if the method obtains better analytic results, efficiency is improved.

Countercurrent chromatography (CCC) is a proven method to isolate proteins from complex mixtures, such as, cell supernatants and natural product extracts in one step. Early on, CCC was reported as effective for fractionating very large proteins, such as, immunoglobulins. Mass loading is greater for the volume of the system than gel filtration chromatography. Since CCC is scalable, CCC can be engineered into flow-through systems eliminating other large volume batch steps.

Substances are separated according to K value (partition or distribution coefficient) in a two-phase solvent system. That is measured as the ratio of concentration in the upper to lower phase (Cu/Cl). In CCC, K is the stationary concentration to mobile phase (Cs/Cm) which can be calculated from the elution volume, as either upper or lower phase can be the mobile phase. Thus, Ks/m calculated from the elution of a compound is the ratio of the elution volume of the chromatographic peak (Vp) minus the excluded volume of the coil to the total volume of the coil minus the excluded volume of the coil.

$$K=(Vp-Vm)/(Vc-Vm)$$

At K=1, the compound elutes at column volume. The phase chosen as the mobile phase is that giving a partition coefficient close to 1. The elution volumes of around 0.5 to 1 comprise the maximal resolution zone. Thus, for a target compound, a solvent system is developed where K is close to 1. Thus, as described below, the VLP's were measured by protein absorbance, nucleic acid absorbance and PCR activity (titer). The values of K for those parameters can be different but the titer showing elution at around 1 column volume or K=1 is the optimal measurement.

For analysis of results in a separation, efficiency will be determined by use of the conventional gas chromatographic equation, $N=(4R/W)$.

The theoretical plates (TP) or N is calculated from the shape of the peaks. (RS will be also calculated as below). R is the retention volume of the peak maximum and W is the peak width expressed in the same units as R. For preparative separations, the values of N are usually <1000, but the more important relationship is resolution. Resolution between adjacent peaks is given by:

$$RS=2(VR_2-VR_1)/(W_1+W_2)$$

Using that equation and substituting each solute retention volume by the following: $VR=Vm+KVS$, the Vm term on both sides of the equation cancels giving $RS=2(K_2-K_1)Vs/(W_1+W_2)$.

Resolution is proportional to Vs and the difference between K's. That is the advantage of the spiral rotors in having a high stationary phase volume, Vs. High resolution is possible even with N<1000. Resolution is measured in isocratic elution (no gradient) which is the usual mode in countercurrent chromatography and can be adjusted by composition of the solvent system.

Stationary phase (SF) retention measurement is done by filling the coil with stationary phase, beginning centrifugation and then pumping mobile phase through at a flow rate appropriate for the rotor and solvent system. When the solvent front comes through, the excluded stationary phase represents the excluded volume, Vm. Subtracting Vm from the total column volume, Vc, yields the stationary phase volume, Vs. The phase retention is the ratio of the stationary phase volume to the total volume, Vs/Vc. High SF values for polar solvent systems, including ATPS, have been achieved with spiral rotors and are expected to be measured for new solvent systems and rotors.

The countercurrent chromatography process occurs in long tubing with a continuous solvent in-flow and out-flow without a seal; the tubing wound in a coil. That is operated in a planetary centrifuge. Solvents are mixed in certain volume ratios to make two stable immiscible phases. In CCC, a solvent system can be devised that can fractionate the sample, removing impurities or separating mixtures. Tubing coils or spools centrifuged at 1000 rpm or higher with flow rates at 2 ml, retain 60-80% volume of stationary phase held by the Archimedean screw and mixed by the centrifugal force field.

The solvent systems used are organic-aqueous compositions of rapidly separating phases with high interfacial tension. Solvents can contain, for example, hexane, t-butyl methyl ether, chloroform and so on, or other organic components. With those solvent systems, CCC has served in small molecule separations. For more polar small molecules and peptides, which are soluble and partition well in butyl alcohol solvent systems, the earlier used multi-layer coil rotor does not perform as well. It was found in studies of spiral channels in disks with varying distance or pitch between the flow channels, greater retention of the stationary phase occurred. A stacked set of plastic disks with the spiral flow channel connecting to the next disk was made and separations of peptides solvent system studies were attained. Subsequently, a multiple disk assembly was made of disks, each with, for example, 4 interwoven spirals with increased pitch that increased SF even further (FIG. 1). Finally, a circular frame support was fabricated with channels to hold tubing and radial channels to form 4 loops per layer as tubing was inserted as shown in FIG. 2. That is a spiral tubing support (STS) rotor. The new spiral rotors were found to retain well the polar solvent systems and even the ATPS (aqueous two-phase solvent) systems. That discovery now makes possible separation of small polar and large molecules by spiral CCC. Using computer aided design, the rotor and gear were changed to nylon composite with complex features, such as, guides for tubing and connector holds. The laser sintering process produced a new lightweight rotor which can easily be produced in different sizes. The frame support makes it possible to substitute different types of tubing. Useful features of a CCC rotor are described, for example, in U.S. Pat. No. 8,597,507. That rotor was used for the separation of VLPs using a novel ATPS as described herein.

Interweaved spirals increase distance between the flow channels or pitch 4 times. That served to increase retention of more viscous solvent systems, such as, a polyethylene glycol (PEG)-phosphate aqueous two phase solvent system (ATPS). Large molecules, such as, proteins and peptides were successfully separated using an ATPS. Spirals in a 5 mm thick high density polyethylene (HDPE) disk were further modified with protrusions across a channel with openings on each side. The barriers were to provide a partial barrier to fluid flow, such as, a mixing bead in every other segment (FIG. 3). A rotor of 5 disks was made and used for protein separation with baseline separation of proteins of MW up to 63,000 daltons, 5-6 mg each of cytochrome c, myoglobin, ovalbumin, lysozyme, and bovine serum albumin (which was retained in the column) and a separation of a mix of 5 higher MW proteins, 5 mg cytochrome c, and 20 mg each of human serum albumin, β-lactoglobulin, α-chymotrypsin, and trypsinogen. The results exemplify keen separation of proteins in CCC. That was possible at a flow rate of 0.5 ml/min at 800-1000 rpm using an ATPS.

However, there remains a need to develop materials and methods to separate or to purify virus particles from mixtures.

SUMMARY OF THE INVENTION

New materials and methods, and a new process are described for separating viruses from complex mixtures using countercurrent chromatography. Certain solvent systems are used to enable such separation.

Suitable solvent systems comprise a polymeric carbohydrate and a salt.

Suitable carbohydrates comprise, for example, a polyether, such as, for example, polyethylene glycol. The carbohydrate can have a molecular weight below about 1,000, for example, below about 800, below about 600 and so on, and may have a molecular weight of about 300, about 400, about 500 and so on. The amount of carbohydrate in the solvent can be from, by weight in water, about 5% to about 50%, about 10% to about 40%, about 15% to about 30% and so on.

Suitable salt comprise a sale, such as, a sulfate, a phosphate, a nitrate, a citrate, a carbonate and so on. The anionic entity can be combined with any of a variety of cations, such as, an alkali metal, an alkali earth metal and so on. The amount of salt in the solvent can be from about, by weight in water, 5% to about 50%, about 10% to about 40%, about 15% to about 30% and so on. The salt can have a pH from about 4 to about 10, from about 5 to about 9, from about 6 to about 8 and so on.

BRIEF DESCRIPTION OF THE FIGURES

The following description of the figures and the respective drawings are non-limiting examples that depict various embodiments that exemplify the present invention.

DETAILED DESCRIPTION OF THE INVENTION

Due to the high cost of machining a mixer-settler spiral form in HDPE disks and the problem of leaks around the TEFLON® sheets which are noncompressible, the mixer-settler rotor described in U.S. Pat. No. 7,892,847 was redesigned and built with less expensive materials that would have good functionality. The TEFLON® sheets after being compressed are a cold flow material and do not retain original thickness and after some use, the whole rotor needs to be tightened but it is difficult to retain the liquid seal. A mixer-settler spiral disk rotor was assembled with 5 polycarbonate disks fabricated by injection molding and each packed between softer compressible sheets, such as, elastomer sheets (0.035 in thick and coated with TEFLON®), such as, VITON® (synthetic and rubber products, a trademark of Chemours, Wilmington, Del.), artificial rubber and the like that compress and regain original shaping when pressure, weight or any other compressible force is removed or reduced. In embodiments, each disc can carry three gaskets below in the rotor stack, as compared to a single gasket in the prior art. Hence, a rotor of interest can include at least two, at least three or more gaskets below a disc.

Hence, of the plural gaskets, one may be placed or situated about center screws of the rotor to control fluid flow down a central void, such as, a shaft, centrally situated in a rotor. Another or the same gasket may be placed or be situated to control fluid flow about or through synthetic rubber or elastomer sheets.

Figure 4:
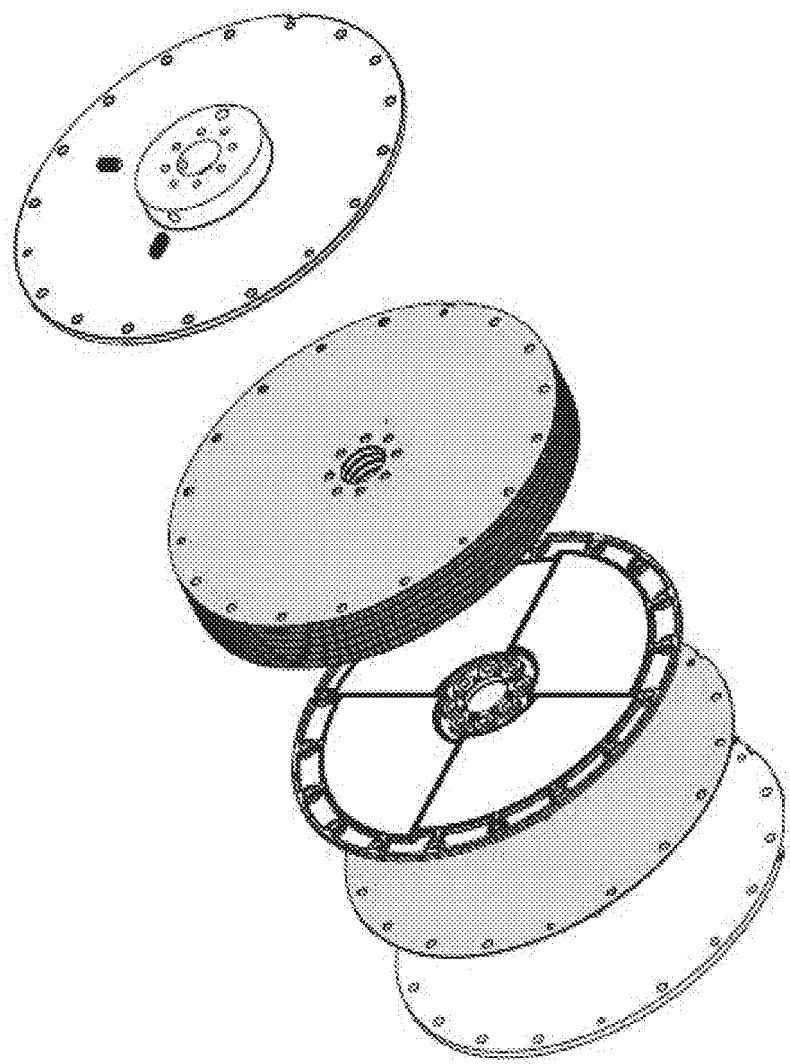
FIG. 4 depicts an exploded view of a stack of components of a rotor.

The improved device for separation and purification of virus particles (as used herein, a virus includes naturally occurring or recombinant forms, such as, virus vectors, VLP's, pseudoinfectious virus-like particles, gutted virus particles and so on, essentially any structure comprising one or more capsid proteins that may or may not comprise an expressed nucleic acid) was a modification of the device described in U.S. Pat. No. 7,892,847 (herein, the '847 patent.) The rotor is made of stacked spiral grooved disks where solvents flow to separate molecules. The groove ends in a hole that allows the liquid flow to move to the next disk. In one type, there are 4 interleaved (interwoven) grooves which at the end of each spiral, a channel underneath goes to the start of the next groove. The disks are sandwiched between gaskets or septums that keep the flow in the groove. Each disk is shaped as provided in FIG. 4A of the '847 patent. FIG. 4B of the '847 patent shows the cross sectional view of a channel beneath the grooves. FIG. 4C is the underside view of the same disk with the shape of the channel carved from the outer ending of the spiral groove to a center hole #0 that goes through to the next disk. The flow goes through a hole #84 in the septum or gasket in FIG. 5 of the '847 patent. The number of disks and septa are sandwiched between end plates or flanges as pictured in FIGS. 6 and 7 of the '847 patent. Those all together are as in FIGS. 1, 4 and 5.

The spiral disc of the '847 patent was modified to have segments formed by protrusions to hold a device, such as, a bead, a barrier, a wall, a hurdle and so on, in spaces along the flow path. In embodiments, a glass mixing bead is placed in every 4$^{th}$ space or segment. The spiral disks with the complex beaded channels are fitted as item #16 of FIG. 2 of the '847 patent.

The disks of the original patent were made of high density polyethylene and were thick, over 6 mm, with the channel underneath having a 1 mm depth. Thinner disks with rims were made as replacement. The thinner discs were not uniformly thick but had rims around the channel shaped underneath. A septum was made of a compressible material, such as, VITON®. When assembled the compressed material, such as, VITON®, blocked flow. To address that issue, another septum was cut with a slit open beneath the channel. That allowed the liquid to flow through to the next spiral and from one disk to the next.

Figure 1:
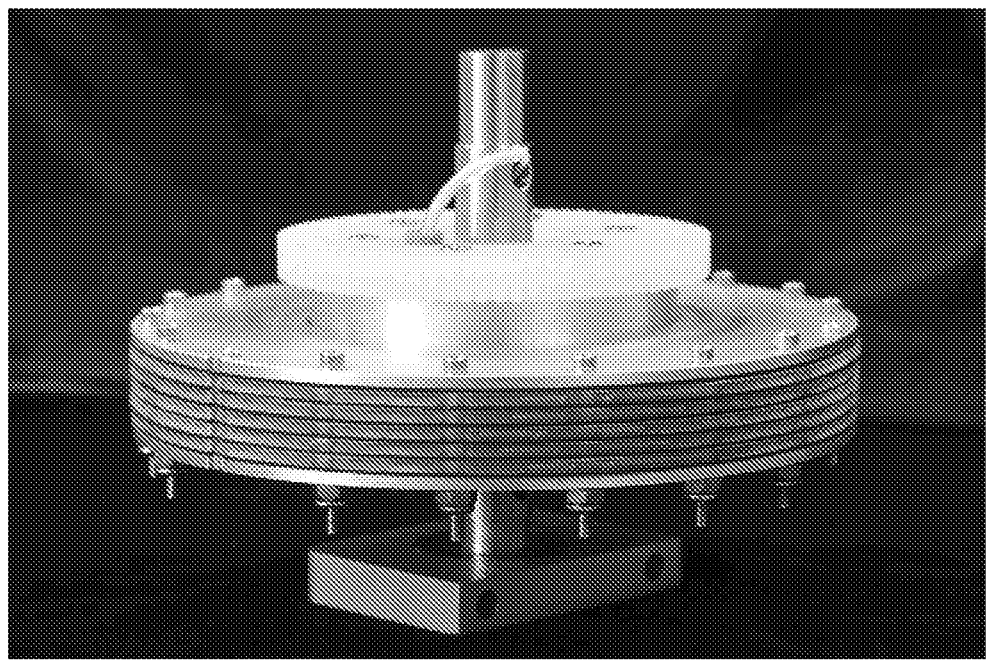
FIG. 1 depicts a stack of disc for performing centrifugal or countercurrent chromatography for separating molecules.

FIG. 1 depicts an assembled rotor with the black VITON® sheets between the clear colored polycarbonate disks which are 3 mm thick at the edges and around holes for the screws. Many disks can be continued to be made from the mold thus the unit cost is lower. These disks also have 4 interweaved spirals that are serially connected by channels underneath that provide flow from the end of one spiral to the entry of the next spiral on the disk and then to the disk below through an opening in the gasket.

Figure 2:
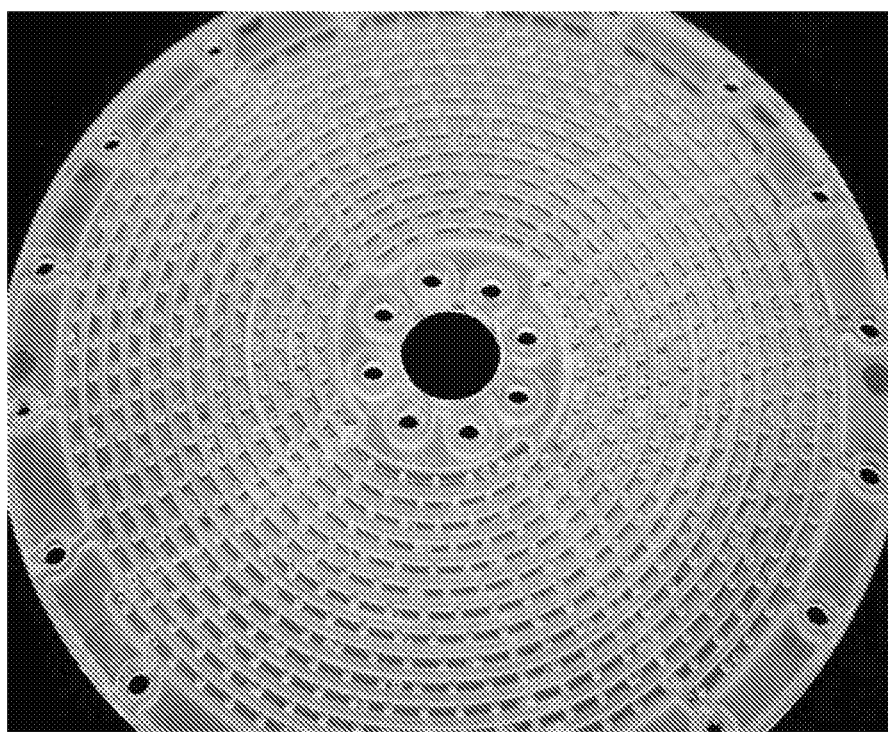
FIG. 2 depicts a disc with glass bead in place.
Figure 3:
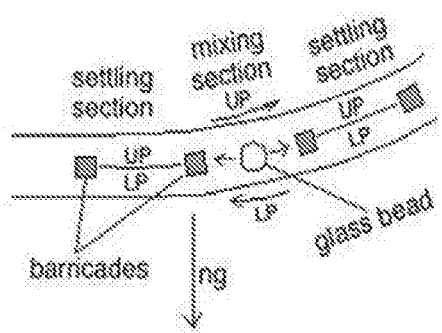
FIG. 3 depicts the orientation of barricades and beads in a portion of a disc.

In the channels are protrusions that hold glass beads to provide mixing and empty spaces to allow adequate settling of the viscous phases of the ATPS. The depiction of a plastic disk with glass beads in place is shown in FIGS. 2 and 3. Also seen are the 4 straight underneath channels that are visible through the plate. The spiral channels are 3 mm wide and 2 mm deep.

Figure 5:
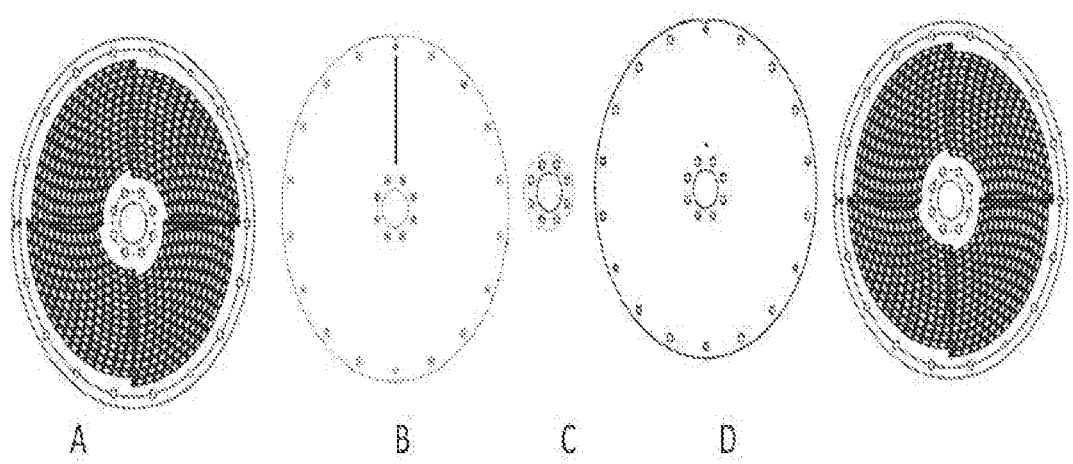
FIG. 5 depicts components of a rotor of interest.
Figure 6:
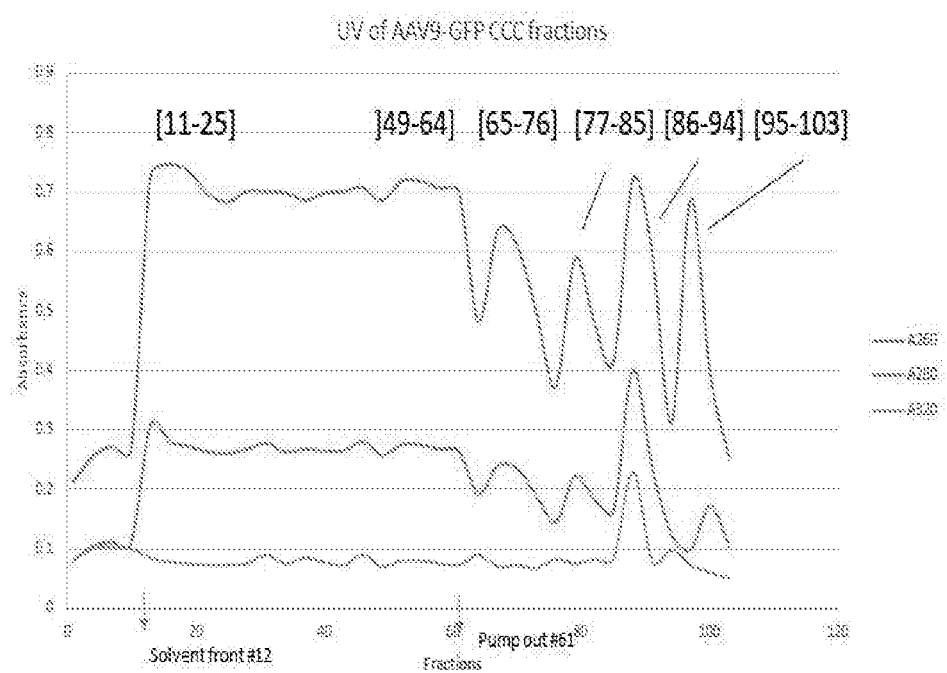
FIG. 6 depicts an absorbance scan of eluted material.

The mechanism of the retention of the stationary phase is depicted in FIG. 3. A plastic disk drawing with the 4 spirals and barricades and how it is arranged in the assembly is shown in FIGS. 4 and 5.

As a result of that development, the mixer-settler CCC rotor is significantly thinner than the original prototype and easy to assemble with the aluminum end flanges and flexible septums that can be aligned with the screw holes lined up with the edge indentations (left edge of rotor, FIG. 1). The soft septum can be tightened and returns to original shape when loosened. Thus, there are no leaks when all is tightened evenly around the rotor. The end user can assemble the rotor easily with parts supplied.

With that CCC rotor, protein analytical and preparative separations are possible with ATPS, the heavy alcohols and new solvent systems, such as, the very polar ethanol-saturated ammonium sulfate solvent. Complete recovery of samples is possible and baseline separations can be developed for any protein sample mix. Suitable solvents include PEG, for example, having a size from about 6000 to about 8000 molecular weight, dextran, for example, having a size from about 60,000 to 70,000 molecular weight and the like. Solvents are selected for beneficial flow and separating properties of the sample analytes. Surfactants can be included in the solvent system, such as, sodium dodecyl sulfate (SDS), or other sulfates, such as, sodium cholate (SC), sodium deoxycholate (SDC) and the like. The amount of surfactants is a design choice to facilitate separation.

U.S. Pat. No. 8,597,509 provides for a rotor that houses multiple coils of a tubing within which solvent and solutes reside and are separated. As provided in the '509 patent, a method of performing countercurrent chromatography to separate substances is provided. "Substances" as used herein includes chemical substances, small organic molecules and biological materials such as DNA, polynucleotides, oligonucleotides, protein, polypeptides, polysaccharides, oligosaccharides, lipids, combinations thereof and so on, as well as larger particles, such as, viruses, VLP's, viral vectors and so on.

The method of performing the countercurrent chromatography comprises (1) providing a test sample and solvent system, (2) routing tubing through an inlet, spiral and radial channels and an outlet, (3) loading said test sample into said solvent system, (4) placing said combined test sample and solvent system into the apparatus, and (5) rotating the apparatus in a centrifuge for a period of time and at a specified speed. Any type of flexible tubing may be used including, but not limited to: (1) TEFLON®, (2) fluorinated ethylene propylene, (3) silicone, (4) stainless steel, (5) TYGON® (TYGON® is a registered trademark of Saint-Gobain Corporation, Solon, Ohio and relates to a range of plastic tubing), (6) crenellated, (7) convoluted. (8) any commonly used flexible tubing, or (9) any tubing that includes a combination of any of the aforementioned materials.

The tubing also can be one which has an irregular or non-uniform inner surface. The irregularities can be obtained by using a commercial tubing manufactured in that manner or by manually manipulating the tubing, such as by crimping the tubing, bending the tubing, folding the tubing and so on, to form an introduced imperfection in the tubing, and particularly by disrupting the smooth inner surface of the tubing to form a non-uniform or irregular inner surface in the tubing.

Application or coating of TEFLON®, liquid polyethylated glycol or similar material may be used wherever tubing is likely to encounter any type of friction or abrasion. The manufactured apparatus may be used in any type of centrifuge, such as, one with a planetary rotation. The spiral tube support also may require one or more weights for balance.

Solvent systems that can be used include, but are not limited to the following: (1) two-phase aqueous polyethylenes and salt solutions; (2) two-phase heavy alcohol aqueous solutions: (3) PEG (MW 1000) 12.5%-$K_2HPO_4$ 12.5%; or a 1:1 (v/v) solution of sec-butanol-1% trifluoroacetic acid.

In embodiments, the invention comprises a countercurrent chromatography disc, rotor or plate comprising a first and a second surface, wherein said first surface comprises a plurality of spiral channels or grooves, to house a tubing, which are interweaved or interleaved to provide plural spiral pathways on a disc. The first surface contains four or more radial channels to provide paths to course tubing and to direct fluid to another spiral pathway. An increase in the number of radial channels per disc quadrant increases stationary phase retention by having fewer return tubing sections crossing flow tubing, enabling more lengths of tubing per disc. The radial channels can have curved ends to minimize tubing having to traverse sharp bends, see, for example, U.S. Pat. No. 8,597,509.

The four or more curved radial channels comprise a generally straight central or middle portion with curves at the termini, where curved includes a sinusoidal configuration, an "S" configuration, a reversed "S" configuration and so on to facilitate tubing placement and seating, for example, to avoid sharp bends and crimps in the tubing.

The curvature can be of a degree or extent so that tubing is aligned to enter the appropriate spiral channel with minimal acute bends to form the interweaved spirals of tubing.

The solar and planetary shafts of the centrifuge can be oriented vertically so that rotor motion is in a horizontal plane. That orientation can enhance attaining phase equilibrium, such as, with viscous solvents, and provides equivalent gravitational force across the rotor. Alternatively, shafts can be horizontal and the CCC STS rotor moves in a vertical plane. That configuration can be more stable in mechanical design.

In embodiments, the countercurrent chromatography plate or disc is comprised of a plurality of interweaved or interleaved spiral channels. A disc or rotor can comprise 4, 6, 8, 12 or more interleaved spiral channels. The channels can be any depth as a design choice, for example, about 4 cm, about 5 cm, about 6 cm, about 7 cm, about 8 cm, about 9 cm, about 10 cm or deeper. Greater channel depth increases the amount of tubing contained in a rotor.

Thus, a single tubing can be configured to form a series of interweaved spirals. For the purposes of the invention, interweaved is considered synonymous with interleaved, and also is synonymous with having a series of spirals in register or where a series of spirals is nested. The rotor contains two access points for ingress and egress of the tubing for a rotor of interest.

Any known and/or commercially available tubing, of any composition as a design choice, or any size, as a design choice, can be used. Thus, channel width can be between from about 0.5 mm to about 10 mm, from about 1 mm to about 9 mm, from about 2 mm to about 8 mm, from about 2.5 mm to about 7.5 mm, about 5 mm, about 3.5 mm, about 2.5 mm and so on Radial channels can have the same size dimensions.

The spiral tube support (STS) or disc can be formed from a variety of materials including, but not limited to, one or more of the following: (1) a nylon, (2) a plastic, (3) a polytetrafluoroethylene, (4) a polyvinyl chloride, (5) a polystyrene, (6) a polyamide, (7) a photopolymer, (8) a FULLCURE® (FULLCURE is a trademark of Objet Geometries Ltd, Rehovet, Ill., and relates to a series of proprietary photopolymers suitable for 3-D printing) material, (9) a PolyJet 3D printer material. (10) a monomeric polymerizable powder, (11) a particulate comprising a metal or a metal composite, and so on, or a combination thereof.

The aforementioned materials can be used to create a hard surface. To create a flexible structure, a material, such as, TangoBlack (TangoBlack is a flexible 3-D printing elastomer) can be used in, for example, a PolyJet 3D printer.

The advantages of using an easily formed material are that a spiral tube support may be quickly and cost effectively fabricated and design changes can be accommodated easily. The prior art teaches construction of spiral tube supports by drilling, milling, machining and so on the spirals out of metal which is substantially more laborious to manufacture, but provides a more durable product, for use, for example, with certain solvents or at higher rotational speeds.

In embodiments, the rotor is formed using a three-dimensional prototyping or printing device (3-D printer) or by additive manufacturing. Examples of a machine that can be used to form the material for the design of the spiral support include, but are not limited to a Sinterstation 2300 Plus (3-D Systems, Rock Hill, S.C.), an Eden500V (Objet Geometries, Rehovet, Ill.), or an EOS Precision (Krailling, Del.). Generally, a polymerizable or fusible finely divided particulate or powder is distributed in a thin layer on a platform, the distributed monomer or compound is exposed to a joining, solidifying, fusing or a polymerizing energy, a next layer of powder is applied to the treated layer, and those processes are repeated until a final structure is obtained. The placing of powder on a solidified layer depends on the shape of the structure at that layer or level. The applied energy can be from a laser, an ultraviolet light, a heat source, a source of different wavelengths of electromagnetic radiation and so on.

A rotor of interest is generally cylindrical or circular in shape with an increased approximate diameter of at least about 22 cm, at least about 24 cm, at least about 26 cm, at least about 28 cm, or larger, such as, about 22.5 cm, about 23 cm, about 25 cm and so on, and a height or depth of at least about 10 cm, at least about 11 cm, at least about 12 cm, at least about 13 cm, or taller.

Tubing can be laid from the bottom of the frame in a channel. Tubing then is passed across a radial channel where it is guided to fit into a next spiral channel that is one in from the outside. The tubing crosses the radial channel into the channel that is one channel in from the outer circumference. That is repeated to fill each spiral channel until at the center, then the tubing is passed through a radial opening or channel to the periphery and then passes through the outer circular channel on top of the spiral formed beneath. The tubing then is routed out an access port to the shaft and out of the centrifuge.

Winding can be in either the clockwise (CW) or counterclockwise (CCW) direction, with a suitably configured rotor, as tubing direction and rotor rotation direction can be varied to enable and to maximize separation of a molecule, particle or entity of interest.

Tubing in the channels may be pressed into a walled first surface space to accept plural layers of spirally oriented tubing, that is, to fit more layers in the rotor, frame or disc. A tool can be used to guide or to push down tubing into the channels. That flattening of the tubing allows more layers of tubing in the rotor, which can provide for greater separation.

Thus, to enhance the flow path, the instant rotor enables a stacking of layers of interweaved spiral layers. Hence, an STS rotor can contain two layers, three layers, four layers, five layers, six layers, seven layers, eight layers, nine layers, ten layers, eleven layers, twelve layers, thirteen layers, fourteen layers, fifteen layers and so on of interweaved, nested spirals of tubing. The tubing can be wound from the bottom in a counterclockwise direction.

Larger bore tubing can be used to enhance tubing volume to enhance separation yield. Hence, for example, tubing inside diameter (ID) can be 1 mm or more, 1.2 mm or more, 1.4 mm or more, 1.6 mm or more, 1.7 mm or more, 1.8 mm or more, 1.9 mm or more, 2 mm or more, or larger in diameter. Tubing can have an ID of at least about 0.9 mm, at least about 0.95 mm, at least about 1 mm or larger in diameter.

Using a tubing with an inner diameter (ID) of about 1.6 mm, the tubing volume of the stack of layers or loops of tubing in a rotor can be at least about 450 ml, at least about 475 ml, at least about 500 ml, at least about 525 ml, or greater volumes. Volume of fluid within a tubing can depend on the inner bore of the tubing, length of the tubing and so on, which can depend on rotor size.

Any known flexible tubing, such as, chromatography tubing, that is virus inert (does not interact or bind a virus), including, but not limited to:
(1) TEFLON® (TEFLON® is a trademark of Chemours, Wilmington, Del. and is a polytetrafluoroethylene thermoplastic polymer than can be constructed as a membrane or other forms), (2) fluorinated ethylene propylene (FEP), (3) stainless steel,
(4) crenellated, (5) convoluted, (6) any commonly used flexible tubing, (7) a polyether ether ketone (PEEK), (8) a polytetrafluoroethylene (PTFE) or (9) any tubing that includes a combination of any of the aforementioned materials can be used as a design choice.

An accommodating centrifuge can have a revolution radius (distance between the solar axis and the planetary axis) increased from about 10 cm to about 13 cm. The revolution radius can be at least about 13 cm, at least about 14 cm, at least about 15 cm, at least about 16 cm, or greater.

A centrifuge of interest can be operated at higher speeds, for example, about 1000 rpm or greater, about 1100 rpm or greater, about 1200 rpm or greater, about 1300 rpm or greater, or at higher speeds.

With the revolution radius incrementally increased from about 10 cm to about 13 cm, with a concomitant increase in disc size of about 5 cm in diameter, from 17.5 cm to about 22.5 cm, and speed increased from 840 rpm to 1200 rpm, for example, the relative centrifugal field (RCF, a function of revolution radius and speed) is increased from 79 g to 209 g, a greater than 2.5× increase. RCF can be increased about 2×, about 2.25×, about 2.75×, about 3×, about 3.5×, about 4× or more.

Relative centrifugal field can be calculated using the formula, $RCF = 11.17 \, r \times (RPM/1000)^2$, where r is the revolution radius in centimeters.

In embodiments, each disc can be associated with two, three or more, gaskets above and/or below a disk in a rotor stack. Hence, a rotor of interest can include at least two, at least three, at least four or more gaskets above and/or below a disc.

A rotor can be constructed so that the lower face of the rotor that engages, abuts, sits on and the like, a shelf of a shaft of interest, can comprise parts which engage complementary sites of the shelf, an accommodating void, such as, a rectangular void on an inferior rotor face in register with and which engages a protruding bar structure of a shaft. Such an engaging affixes a rotor to a shaft.

The planetary shaft also can be designed to comprise a flare in size that increases in diameter in the direction away from the rotor to provide greater support of the larger and heavier rotors.

The rotor frame securing a rotor in a centrifuge can be machined from a strong, yet light, material, such as, a metal, such as, aluminum; can be molded, such as, a ceramic; can be printed using a 3-D printer using suitable particulate starting materials and so on, as known in the art, and as a design choice. At higher centrifuge speeds, metal may be preferred for constructing a rotor and a centrifuge.

At movable joints of the shafts, sealed, pre-lubricated or self-lubricating roller bearings can be employed, such as, at or in the juncture of the shaft and a shaft housing; at or in the juncture of a shaft and a shaft collar and so on. Such sealed bearings are suitable for high radial load and minimize angular misalignment at high speed. Increased rotor size and weight are better accommodated with such bearings.

Such devices provide a secure seating and connection of a rotor on a shaft, and enable free movement on the rotor frame about the central shaft.

A centrifuge of interest can comprise a power unit to provide the circular motion of the shafts, for example, an alternating current (AC) motor to enhance speed control. That provides controlled acceleration and deceleration, variable operations at low and high speeds, high torque and movement in either direction. The power unit can be attached directly to a shaft or spindle or can be attached indirectly to a shaft or a spindle, for example, by a belt, a chain and so on, as known in the art.

A centrifuge of interest can be in an enclosed cabinet and can comprise a refrigeration unit or device to lower the temperature under which separation occurs.

A centrifuge of interest can comprise a heat sink to control operating temperature.

The centrifuge of interest can accommodate greater fluid flow rate, greater than the currently standard rate of 2 ml/min, such as, greater than 3 m/min, greater than 3.5 ml/min, greater than 4 ml/min or higher flow rates. Fluid flow is attained and maintained using pumps known in the art.

The increased throughput of a centrifuge of interest enables separation of larger amounts of sample, such as, greater than 10 g of sample, greater than 20 g of sample, greater than 30 g of sample, greater than 40 g of sample, greater than 50 g of sample or larger amounts of sample.

Fitted tubing space, which is the ratio of space occupied by tubing in channels (rotor volume less the center shaft space) was increased by a factor of about 3.5. Fitted tubing space can be increased by a factor of 3, 4, 4.5, 5, 5.5, 6, 7, 8, 9, 10 or more.

Choice of a beneficial solvent system is essential to obtaining separation or isolation of a desired entity or entities. A factor to be considered is determining the relative partition ratio ($K_D$) of an entity between two phases of a solvent system or mixture.

Partition coefficients (K) of individual viruses can be measured by spectroscopy, HPLC, UV spectroscopy, fluorescence and other descriptive techniques as taught herein or as known in the art. An assay which detects a physical property of a virus, a viral vector a VLP and so on, can be used, such as, a sizing assay, a visualization assay and so on, as well as a functional assay, such as, virus titer, expression of a transgene and so on.

Solvent systems of different separation methods may be similar in composition. However, because the principle or mechanism of separation between or among techniques or technologies varies, what operates for one device does not guarantee operability of that solvent in another device. Hazecamp et al. (J Liq Chrom Rel Technol 27(15)2421-2439, 2004) teach a yield of only 3.1/% using a solvent comprising a hexane. The CPC process of US Publ. No. 2018/0036278 relates to use of a solvent of cyclohexane, heptane or octane. Any solvent system must be reviewed theoretically and actually tested in a CCC device.

The K of a target compound for facile separation can be about 0.3 or greater, about 0.325 or greater, about 0.35 or greater, about 0.375 or greater, about 0.4 or greater, about 0.425 or greater, about 0.45 or greater, about 0.5 or greater, about 0.55 or greater, about 0.6 or greater, about 0.65 or greater, about 3 or lower, about 2.75 or lower, about 2.5 or lower, about 2.25 or lower, about 2 or lower, about 1 or lower, or lower.

For adequate resolution of compounds to avoid overlap between or amongst adjacent collected fractions, the separation factor of two entities, 1 and 2, according to the formula, $\alpha=K_2/K_1$, wherein $K_2>K_1$, can be greater than 1.5, greater than 1.6, greater than 1.7, or more, although larger SF values could translate to a larger amount of fractions not containing virus.

It can be beneficial if each phase of the solvent system be present in about equal volumes, but not necessary.

Suitable solvent systems comprise a polymeric carbohydrate and a salt.

Suitable carbohydrates comprise, for example, a polyether, such as, for example, a polyethylene glycol. The carbohydrate can have a molecular weight below about 1,000, for example, below about 800, below about 600 and so on, and may have a molecular weight of about 300, about 400, about 500 and so on. The amount of carbohydrate in the solvent can be from, by weight in water, about 5% to about 50%, about 10% to about 40%, about 15% to about 30% and so on.

Suitable salts comprise a state, such as, a sulfate, a nitrate, a citrate, a carbonate and so on. The anionic entity can be combined with any of a variety of cations, such as, an alkali metal, an alkali earth metal and so on. The amount of salt in the solvent can be, by weight in water, from about 5% to about 50%, from about 10% to about 40%, from about 15% to about 30% and so on. The salt can have a pH from about 4 to about 10, from about 5 to about 9, from about 6 to about 8 and so on.

The lower or heavier phase of a two-phase solvent system can be introduced from the inner entry point. Alternatively, the upper or lighter phase of a two-phase solvent system can be pumped via the outer entry point with the appropriate orientation of the spiraling on the rotor, and hence, the tubing, and the appropriate direction of rotation by the centrifuge.

Spiral coiled tubing-rotors or spiral disc rotors can be operated at a speed and at an MP fluid flow rate as design choices, for example, which provide maximal separation of molecules with retention of the stationary phase SP. Hence, a flow rate can be about 2 ml/min or greater, about 2.25 ml/min or greater, about 2.5 ml/min or greater, about 2.75 ml/min or greater, or at greater flow rates. A centrifuge can be operated at a speed of about 700 rpm or more, about 800 rpm or more, about 1000 rpm or more, about 1200 rpm, or faster.

Spiral tubing support or spiral disk rotor designs of interest enable a means to chromatograph virus in an automated system. A laboratory instrument system can consist of a planetary centrifuge with one or more STS rotors, a pump, sample loading valve, fraction collector and a system controller via computer or mobile phone app. Time of a run, with settings of rpm, pump solvent delivery selection and flow rates, automatic sample injection and fraction collection time can be programmed as a design choice. Rotor and components of interest provide a new useful separation means for materials of the virus market.

After fractionating a composition (e.g., after a single run of a process above), separated entities may overlap partially in fractions between the concentrated peaks of separated entities or particles, even in an amount that is not readily detectable. To recover more pure virus, dried fractions that are resuspended n the solvent system can be used in a second run of a separation process of interest, and so on, until more pure population of virus is obtained. That could result in a population with a purity of about 100%, greater than or equal to about 95%, greater than or equal to about 90°, greater than or equal to about 85% pure. By, “about,” herein is meant a metric that can vary up to 05% from a stated value, but no greater than an absolute, for example, about 100% cannot exceed 100%.

A fraction or a separated compound is removed from a rotor and can be subjected to further processing, such as, removal of solvent, replacement of diluent and so on, practicing known methods, such as, dilution, washing, centrifugation, evaporation, lyophilization and so on to obtain a purified preparation of virus.

Materials for making a rotor or disc of interest are provided herein or are available commercially, for example, components can be machined; or components, such as, discs or rotors, can be purchased, for example, from CC Biotech (Rockville. Md.). Planetary centrifuges can be made as known in the art or can be purchased. Tubing and chemical reagents are available commercially.

The technology is capable of separating viruses, any virus particles, such as, adeno-associated virus (AAV). As viruses are particulate structures of certain molecular weight, any virus can be purified by CCC and an aqueous two-part solvent. Examples of suitable viruses are plant viruses, animal viruses, insect viruses, retroviruses, lentiviruses, adenoviruses, bacteriophage, alpha viruses, flaviviruses, immunodeficiency viruses, SV40, Dengue virus, measles virus and so on.

For example, AAV is an icosahedral virus of 20-26 nm diameter size with a single-stranded DNA genome of 4.6-6 kb. Since AAV virus particles (VP) are not integrated in the host genome, AAV are a useful tool for gene delivery into a wide variety of cell types and reduced immunogenicity. Recombinant AAV (rAAV) vectors contain no pathogenic genes; and inverted terminal repeats (ITR) minimize self-replication. The ‘gutless’ rAAV has been FDA evaluated as a safe vector for use in human genetic therapy. The rAAV vector with green fluorescent protein (GFP) protein has been used in the experiments. The purification process has involved density gradient centrifugation using iodixanol and column chromatography, such as, ion exchange and SEC. The virus is relatively heat stable and can be separated from other viruses and Adeno helper virus in the purification process. The need is to have high amounts of $10^{13-14}$ particles for a therapeutic dose. A problem is dilution that occurs with current purification steps. Thus, a streamlined purification process is a goal to produce a higher recovery of purified virus.

AAV can be produced by transfection of 293 T cells (ATCC) using pAV-FH AAV vector, an adenovirus helper vector and a vector encoding the rep and serotype-specific cap. The DNA can be introduced into the cells by transfection with for example, polyethylenimine (PEI 25K, Polysciences). After 72 h of incubation at 37° C., the cells can be harvested. The viruses in cell culture supernatant and cell pellets will be separately precipitated by NaCl and PEG8000. Alternately, the cell culture supernatants and the sonicated suspension of cell pellets could be combined and precipitated using 50% of saturated ammonium sulfate. A pretreatment step using 30% of saturated ammonium sulfate will facilitate to remove host cellular proteins and reduce sample volume. The precipitates can be suspended in phosphate-buffered saline (PBS) and combined, and used as virus crude sample for loading into the CCC centrifuge For quality assessment of isolated AAV particles, the physical and functional titer, identity and purity of isolated AAV virus can be analyzed. The physical titer can be determined by quantitative PCR, for example, using SYBR green dye (Thermo Fisher Scientific). Viral genome copy (GC) number in a 1 ml sample can be calculated from a standard curve generated from serial dilutions of a plasmid stock (ITR-containing plasmid, Addgene). To determine functional activity of isolated AAV vectors, ability of isolated AAV virus to infect 293T cells can be assessed. For example, serial dilution of isolated AAV vectors can be added to pre-plated 293 T cells, and the transgene protein expression can be measured at 48 h following transduction. Identity and purity of isolated AAV particles can be determined by electrophoresis on 8-20% SDS polyacrylamide gels followed by silver staining. The test can examine for presence of viral capsid proteins, VP1, VP2 and/or VP3, in the correct stoichiometry, consistent with AAV, and for the absence of visible protein contaminants from host cells or cell culture medium components.

A two phase aqueous solvent was used. The solvent can comprise an organic solvent, colloids, polysaccharides and so on, and any of a variety of salts. For example, various sizes of polyethylene glycol (PEG) can be used. A phosphate, a sulfate, a citrate and so on salt can be used. Various combinations can be used as the upper or lower phase, as the mobile or stationary phase.

For example, a suitable PEG is a PEG 400. A suitable salt is sodium citrate at about 20% concentration.

Materials for making a rotor of interest are provided, for example, in U.S. Pat. No. 7,892,847 or 8,597,509, and components can be machined, and are available from CC Biotech (Rockville, Md.) or components are available commercially.

The rotor is used essentially as known in the art, for example, as provided in U.S. Pat. No. 7,892,847 or as provided herein.

The invention now will be exemplified in the following non-limiting examples.

EXAMPLES

Example 1 Determining a Suitable Solvent System

A two phase solvent system was developed by adapting solvent systems used in protein extraction experiments and mixing the components to make two immiscible phases. Solutions of AV9-GFP virus particles (Vector Labs, Malvern, Pa.) were added to potassium phosphate/polyethylene glycol (MW 3350, PEG 3350) two-phase solutions, such, the following. The UV absorbance, as measure of the distribution of protein, was determined and is in column 2 of the table.

TABLE 1

| Solvent, by weight in water containing VLP's | Partition ratio [upper phase/lower phase] abs. 280 nm |
|---|---|
| A. 12.5% PEG 3350 12.5% KH$_2$PO$_4$ | 2.3 |
| B. 12.5% PEG 3350 6.25% KH$_2$PO$_4$/6.25% K$_2$HPO$_4$ | 3.6 |

The preferred partitioning ratio of the VLP's is about 1. If partitioning of VLP's is close to 1, then the values mean the VLP's could be separated from the bulk of the protein and other materials which would move out later than the particles with the mobile lower phase in CCC. Since the VLP's are concentrated from the cell culture by ammonium sulfate precipitation, a two phase solvent composition with PEG 3350 and sat. ammonium sulfate was developed. The following stock solutions were combined in the volume ratios as listed to form a two phase solution with equal volume upper phase to lower phase

TABLE 2

| Stock solution | ml combined [volume ratio] |
|---|---|
| 25% PEG 3350 by weight in water | 3 |
| sat. ammonium sulfate | 1 |
| VLP's in PBS [VLP's precipitated and suspended in PBS] | 1 |

UV absorbance of each phase was measured and the titer (GC) was determined of each phase and the results are listed in the following table.

TABLE 3

| Phase | Abs units 260 nm | Abs units 280 nm | Abs units 320 nm | Titer (GC/mL) |
|---|---|---|---|---|
| UP | 0.438 | 0.378 | 0.044 | $1.88 \times 10^{11}$ |
| LP | 15.62 | 13.2 | 6.36 | $4.5 \times 10^{13}$ |

The partitioning of everything is far less than 1 (K<<1) with all distributed in the lower phase. Absorbance at 260 nm designated nucleic acid content and 280 nm is a measurement of protein concentration. The 320 nm is a baseline, background, and a measure of turbidity.

Viral particles are studied with PEG 400 (MW=400) with partitioning into the upper phase, intermediate phase and lower phase with adjustments in salt content and pH. Some solutions, such as the following formed two equal phases.

TABLE 4

| 70% PEG 400 (ml) | 40% PO$_4$ pH 7.4 (ml) [77 g K$_2$HPO$_4$, 23 g NaH$_2$PO$_4$, 150 g H$_2$O] | 25% NaCl (ml) | Water (ml) | Separation time (sec) | Volume (ml UP, ml LP) |
|---|---|---|---|---|---|
| 1.05 | 1.625 | 1.2 | 0.125 | 67 | 2, 2 |
| 1.05 | 1.625 | 0 | 1.325 | 59 | 2, 2 |

A solution of 20% PEG 400 and 20% sodium citrate formed a 1:1 volume ratio of two phases. Another composition of two equal phases was 26.67% PEG400 and 18.67% Na$_3$ citrate.2 H$_2$O.

The following stock solutions were made and measured distribution of protein and viral like particle activity in each were determined.

TABLE 5

| Solution | Composition wgt % in water |
|---|---|
| A | 70% PEG 400 |
| B | 25% NaCl |
| C | 35% $Na_3$ citrate 2 $H_2O$ |

Examples of solutions formed with amounts of those stock solutions combined are as follows.

TABLE 6

| A 70% PEG 400 (ml) | B 25% NaCl (ml) | C 35% Na citrate (ml) | Water (ml) | Separation time (sec) | Volume (ml UP, ml LP) |
|---|---|---|---|---|---|
| 1.14 | 1.2 | 2.29 | 0 | 180 | 1.4, 3.2 |
| 1.14 | 0 | 2.29 | 0.57 | 148 | 1.9, 2.1 |

The solvent systems in Table 7 below were made with adjustment of the sodium citrate pH and after determination of the virus particle titer. The lower phase showed no measurement (column 6), so the solvent was changed for both phases with a centrifuge filter concentrator and adding another solvent.

There were useful distributions of K with respect to the titer listed in the last column of Table 7.

TABLE 7

| Two phase solvent system (volume ratio UP to LP about 1:1 after equilibration) | | DNA 260 nm | Protein 280 nm | K, s/m = U/L UP/LP (280 nm) [260] | Titer (GC/ml) | Change Buffer Titer | K Titer s/m |
|---|---|---|---|---|---|---|---|
| #1] PEG 400/sodium | UP | 0.388 | 0.493 | 9.86 [4.4] | 1.11 × $10^{10}$ | 4.25 × $10^9$ | 0.6 |
| citrate/sample (pH = 7.0) | LP | 0.088 | 0.05 | | — | 7.38 × $10^9$ | |
| #2] PEG 400/sodium | UP | 0.58 | 0.673 | 9.21 [3.4] | 1.68 × $10^9$ | 4.35 × $10^9$ | 1.3 |
| citrate/NaCl/sample (pH = 7.0) | LP | 0.173 | 0.073 | | — | 3.31 × $10^9$ | |
| #3] PEG 400/sodium | UP | 0.461 | 0.566 | 6.51 [2.7] | 1.32 × $10^{12}$ | 9.87 × $10^9$ | 89 |
| citrate/sample (pH = 8.5) | LP | 0.172 | 0.087 | | — | 1.1 × $10^8$ | |
| #4] PEG 400/sodium | UP | 0.699 | 0.708 | 4.37 [2.6] | 4.34 × $10^9$ | 6.01 × $10^8$ | .024 |
| citrate/sample (pH = 5.5) | LP | 0.264 | 0.162 | | 3.47 × $10^{10}$ | 2.47 × $10^{11}$ | |

For sample #1 with a K of 0.6 for upper phase/lower phase, if the lower phase is used as the mobile phase in the chromatography, the target viral particles would come out at 0.6 column volumes or for some fractions after the solvent front; and sample #2, particles would come out later at 1.3 column volumes; sample 3, particles would effectively not move much or come out of the coil; and the sample #4 which had a K=0.024, particles would come out early, at the solvent front. The 280 nm values are averages of proteins, that in all samples, would come out later, after 2 column volumes (samples #3 and 4), for example.

Chromatography could be run in the reverse elution mode with the 1/K value or s/m with s, stationary phase changed to the lower phase and the mobile phase changed to the upper phase. In such case, K is 1.67 and the viral particles will come out at 1.7 column volumes with time for many components to separate. The solvent system with NaCl has a reasonable K=1.3 and 1/K=0.8 such that the run can be done in either direction. The effect of pH is seen in the results as well. The acidic and basic conditions impact partitioning of the titer. Low pH drives activity to the lower phase.

Example 2 Virus Particle Separation

It was considered best to perform a CCC separation with the solvent system of sample #1 and the solvent system was mixed according to Table 6 in 10 times the volume, for example, 114 ml solution A and 229 ml solution C, 57 ml water and no NaCl (second formulation B). The solvent system of sample #2 with 25% NaCl added could be used as well, but starting with fewer components was considered more efficient. The final concentration of PEG 400 and NaCitrate were both 20% in that solvent system. The solvent system was run in 1/K mode with upper phase mobile (CCW rotation with flow into the bottom. U o H elution mode) at a flow rate of 0.5 ml/min and at 800 RPM in the STS-4 rotor. Eluate was collected in a fraction collector with 3 ml per tube.

TABLE 8

| Analyte component | K (expected column volume) |
|---|---|
| 280 nm (protein) | 0.1 |
| 260 nm (DNA) | 0.22 |
| Titer | 1.7 |

The sample was added as the water component to small volumes of the stock solutions as shown in Table 6, the precipitate of the VLP's was suspended in 1.2 ml water and added to 2.28 ml 70% PEG (A) and 4.6 ml 35% Na citrate (C) and the resulting two phase solution was injected via a plastic syringe directly into the inflow tubing. The tubing was connected to the pump and the sample was pumped into the rotor. Then, centrifugation was started and the upper phase was pumped in at 0.5 ml/min. The elution was continued until 180 ml or 360 min when the contents were pushed out by stopping rotation and pressurization with helium. Fractions were continued to be collected until all contents came out. The absorbance was determined of the fractions and plotted in FIG. 6. There were multiple peaks and fractions in each, which were combined and assayed for PCR activity. The fractions pooled are shown in the figure. Table 9 has the data of each combined fraction.

The fractions 86-94 had significant activity and had the highest peak of protein measurement. There was a minor peak after that major peak, possible indication that the VLP's moved in the solvent system and there were other fractions that could be other heterogeneous products. Further analysis, such as SDS PAGE, was done. Specific bands were present in the Pool #5 sample, which were not found in the remaining Pool samples. The fractions could be analyzed for particle diameter measurement by techniques, such as, nanoparticle tracking analysis and multi-angle light scattering.

Table 9 has the data of each combined fractions that are numbered 1 to 6 and plotted in the table.

TABLE 9

Combined fractions and determined titer

| Fraction | titer (GC/mL) | Log | Pool # | Fraction | Log |
|---|---|---|---|---|---|
| F11-25 | 1.36E+12 | 12.13354 | 1 | 11-25 | 12.13354 |
| F49-64 | 91200000000 | 10.95999 | 2 | 49-64 | 10.95999 |
| F65-76 | 3.59E+11 | 11.55509 | 3 | 65-76 | 11.55509 |
| F77-85 | 29400000000 | 10.46835 | 4 | 77-85 | 10.46835 |
| F86-94 | 4.97E+12 | 12.69636 | 5 | 86-94 | 12.69636 |
| F94-103 | 1.23E+12 | 12.08991 | 6 | 94-103 | 12.08991 |

Figure 7:
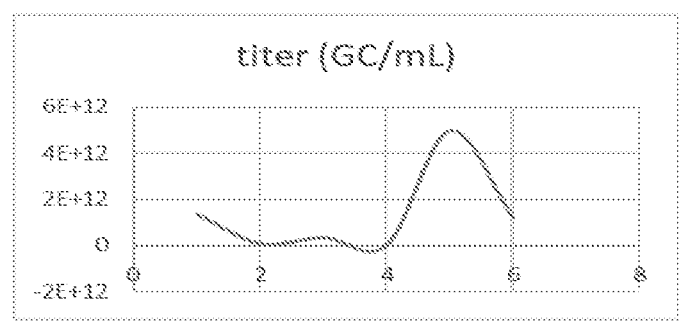
FIG. 7 depicts virus titer of various separated fractions.
Figure 8:
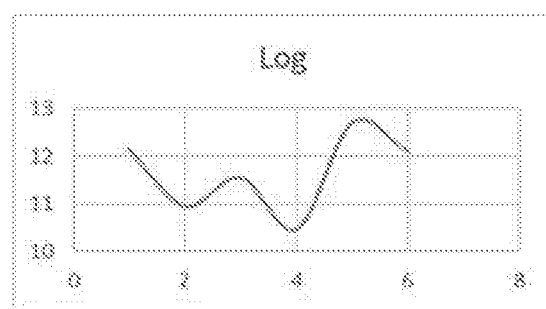
FIG. 8 depicts virus log titer of various separated fractions.

Pooled fraction 5 has the highest titer shown in the titer and titer log plots (FIGS. 7 and 8). Since each fraction is not analyzed before pooling, it is likely that future experiments will find very homogeneous VLP's that have moved in the solvent system where there is still material left behind. Although the elution volume appears to be larger than expected from the K determination, there was much material separated in front and after the highest titer fraction.

Early results show that spiral CCC is a method that can purify virus particles and virus-like particles and the method is capable of separating unfilled capsids and extra nucleic acid strands. The system can absorb more sample mass to provide useful doses of active VLP's for in vivo application. This is the first time a two phase solvent system has been used for VLP's that was able to hold the VLP's in the instrument well after the solvent front and have the target molecules elute in front of other side products. The solvent system would be useful for chromatographing more mass of VLP's.

All references cited herein, each herein is incorporated by reference in entirety.

REFERENCES

Ito, Y. (2005) "Instrumentation for Countercurrent Chromatography", Ewing's Analytical Instrumentation Handbook, 3$^{rd}$ ed. J. Cazes ed. Marcel Dekker, New York, pp. 893-943.
Knight, M. (2006) "Separations of hydrophobic synthetic peptides in counter-current chromatography", J. Chromatogr. A, 1151 (148-152.
Ito, Y., F. Q Yang, P. E. Fitze, and J. V. Sullivan. (2003) "Spiral disk assembly for high-speed countercurrent chromatography." J. Chromatog. & Related Techniques, 26 1355-1372.
Ito, Y. Yang, F.-Q., Fitze, Powell, J., Ide, D. (2003) Improved spiral disk assembly for high-speed counter-current chromatography, J. Liq. Chromatog. A 1017: 71-81.
Knight, M., Finn, T. M, Spiral countercurrent chromatography studies using the spiral disk assembly. Journal of Liquid Chromatography and Related Technologies, (2009) 32: 2669-2685.
Ito, Y. M. Knight, T. M. Finn, Spiral Countercurrent Chromatography, Journal of Chromatographic Science (2013) 51:726-738 doi:10.1093/chromsci/bmt058
Ito. Y., Qi, L., Powell, J., Sharpnack, F., Metger, H., Yost, J. Mixer-settler countercurrent chromatography with a barricaded spiral disk assembly with glass beads, J. Chromatography A. (2007) 1151:108-114
Ito, Y., Clary, R., Sharpnack. F., Metger, H. and Powell, J.: Mixer-settler counter-current chromatography with multiple spiral disk assembly, J Chromatography A, (2007), 1172: 151-159.
Shibusawa, Y., Takeuchi, N., Sugawara, K. Yanagida. A., Shindo, H., Ito, Y. (2006) "Aqueous-aqueous two-phase systems composed of low molecular weight of polyethylene glycols and dextrans for counter-current chromatographic purifications of proteins" J. Chromatog. B, 844 217-222.
Erlanger, B. F. Cooper. A. G., Cohen, W. The Inactivation of Chymotrypsin by Diphenylcarbamyl Chloride and its Reactivation by Nucleophilic Agents, (1966) Biochem. 5: 190-196.
Conway, W. D, (1995) Chapter 1 "Overview of Countercurrent Chromatography" ACS Symposium Series 593 "Modern Countercurrent Chromatography" W. D. Conway, R. J. Petroski, eds. American Chemical Society Washington D.C. pp. 1-14.
Zhang et al. (2014) Analytical Chemistry 86(8)3980-3984.

I claim:

1. A method for purifying a virus particle comprising applying a sample comprising a virus in a two part aqueous solvent (ATPS) comprising a carbohydrate and a salt into a countercurrent chromatography centrifuge comprising a mixer-settler rotor comprising plural discs, each disc comprising a spiral groove forming a solvent flow path, said groove comprising a device therein for mixing said ATPS flowing in said groove, and exposing said rotor to planetary motion to separate said virus from said sample.

2. The method of claim 1, wherein said carbohydrate comprises a polyethylene glycol.

3. The method of claim 1, wherein said salt comprises a sodium citrate.

4. The method of claim 3, wherein said salt comprises a phosphate.

5. The method of claim 3, wherein said salt comprises a citrate.

6. The method of claim 1, wherein said solvent comprises sodium chloride.

7. The method of claim 1, wherein said solvent comprises a surfactant.

8. The method of claim 1, wherein carbohydrate comprises a molecular weight below about 800.

9. The method of claim 1, wherein carbohydrate comprises a molecular weight below about 600.

10. The method of claim 1, wherein carbohydrate comprises a molecular weight about 400.

11. The method of claim 1, wherein carbohydrate comprises from about 10% to about 40% of said solvent.

12. The method of claim 1, wherein carbohydrate comprises from about 15% to about 30% of said solvent.

13. The method of claim 1, wherein salt comprises from about 10% to about 40% of said solvent.

14. The method of claim 1, wherein salt comprises from about 15% to about 30% of said solvent.

15. The method of claim 1, wherein said solvent comprises a solution of salt.

16. The method of claim 15, wherein said solution comprises a pH from about 4 to about 10.

17. The method of claim 15, wherein said solution comprises a pH from about 5 to about 9.

18. The method of claim 15, wherein said solution comprises a pH from about 6 to about 8.

* * * * *